United States Patent [19] [11] 4,279,249
Vert et al. [45] Jul. 21, 1981

[54] NEW PROSTHESIS PARTS, THEIR PREPARATION AND THEIR APPLICATION

[75] Inventors: Michel Vert, Deville-les-Rouen; Francois Chabot, Rouen; Jean Leray, Sevres; Pascal Christel, Paris, all of France

[73] Assignees: Agence Nationale de Valorisation de la Recherche (ANVAR); Institut National de la Sante et de la Recherche Medicale, both of Neuilly-sur-Seine, France

[21] Appl. No.: 85,511

[22] Filed: Oct. 17, 1979

[30] Foreign Application Priority Data

Oct. 20, 1978 [FR] France ................................ 78 29878

[51] Int. Cl.$^3$ ................................................ A61F 5/04
[52] U.S. Cl. .............................. 128/92 D; 128/92 BB; 128/92 BA; 128/335.5; 525/415
[58] Field of Search ................ 525/415; 128/155, 348, 128/335.5, 334 R, 92 BC, 92 D, 92 BB, 92 BA, 92 C; 528/354; 3/1.4

[56] References Cited

U.S. PATENT DOCUMENTS

| 3,463,158 | 8/1969 | Schmitt et al. ........................ 128/334 |
| 3,626,948 | 12/1971 | Glick et al. ......................... 128/335.5 |
| 3,739,773 | 6/1973 | Schmitt et al. .................. 128/92 BC |
| 3,867,190 | 2/1975 | Schmitt et al. ............... 117/138.8 A |
| 3,982,543 | 9/1976 | Schmitt et al. .................... 128/335.5 |

Primary Examiner—Earl A. Nielsen
Attorney, Agent, or Firm—Cushman, Darby & Cushman

[57] ABSTRACT

Osteosynthesis parts are made of an absorbable polymer composition consisting of a matrix of lactic acid homopolymer, or a copolymer very high in lactic acid units, having discrete reinforcement elements embedded therein. The reinforcement elements are made of glycolic acid homopolymer or copolymers predominant in glycolic acid units. Such a composition may be shaped with a minimum of polymer degradation into osteosynthesis parts exhibiting good resilience, shock resistance, and tensile strength.

21 Claims, No Drawings

NEW PROSTHESIS PARTS, THEIR PREPARATION AND THEIR APPLICATION

The present invention relates to new parts for osteosynthesis, as well as their production and their application.

More precisely, the invention relates to osteosynthesis parts, such as plates, screws, nails, pegs and pins made of a bio-compatible, plastic material entirely absorbable in vivo, which are in the form of composite parts. They exhibit sufficient mechanical properties to provide efficacious and reliable support to the traumatized skeleton, for long enough time to allow for the repair and consolidation of fractures, even in the case of long bones. They also exhibit good bio-absorbability, sufficient to permit avoiding a second surgical intervention, such as is frequently required to remove osteosynthesis parts when they are made of metal.

BACKGROUND OF THE INVENTION

The plastic materials, derived from a high molecular weight polyesters of α-hydroxyacetic acid (or glycolic acid), have been described in U.S. Pat. No. 2,668,162, and those derived from the polyesters of lactic acid have been described in U.S. Pat. No. 2,703,316.

The materials based on α-hydroxyacetic acid polyesters (PGA) have been recognized as being bio-compatible, bio-absorbable and capable of yielding bio-absorbable surgical sutures (U.S. Pat. No. 3,297,033).

The utilization of osteosynthesis parts made of hydroxyacetic polyesters (PGA) has been described in U.S. Pat. No. 3,739,773, as well as the reinforcement of these parts by the fabrication of composites with elements that are not absorbable by the organism.

GENERAL DESCRIPTION OF THE INVENTION

The present invention relates to osteosynthesis parts, in the shape of a three-dimensional solid, based on a bio-compatible, absorbable polymer, characterized by the fact that they are in the form of composite parts constituted by a matrix of polylactic acid or by a copolymer of the latter, said matrix containing reinforcement elements, embedded in the matrix, with a base of polyglycolic acid or of a copolymer of the latter, and containing, optionally, a charge capable of stimulating the absorption of the polymer for the benefit of a newly formed tissue.

The osteosynthesis parts of the present invention can also exhibit the following characteristics, singly or in combination:

(1) the polylactic acid constituting the matrix must be of high optical purity so as to possess a high degree of stereoregularity and of crystallinity. A D-lactic acid polymer or, preferably, an L-lactic acid polymer is used. Enantiomorphous purity must be over 90%.

Biodegradable copolymers of lactic acid or of a compatible comonomer may also be used. Representative comonomers include derivatives of α-hydroxy acids, derivatives of α-amino acids, e.g. carboxy anhydrides of α-amino acids such as those of alanine, lactones such as β-methyl propiolactone, etc. The usable copolymers of polylactic acid comprise the stereocopolymers that are copolymers of L- and D-lactic acids. Generally, the copolymers of PLA used are those that contain enough lactic acid patterns to possess a high degree of crystallinity. These copolymers contain, in numbers of patterns, at least 90% and, preferably, 95% patterns derived from lactic acid, in order to be able to keep sufficient mechanical properties for an appropriate length of time after placement of the osteosynthesis part;

(2) the matrix is obtained at the start from a polylactic acid or from a copolymer of the latter, of high molecular weight, such that molecular weight is greater than or equal to 80,000 or, preferably, 100,000;

(3) the reinforcement elements are constituted by a polyglycolic acid, or a copolymer thereof, of high molecular weight such that the molecular weight is greater than or equal to 10,000, and is generally between 10,000 and 100,000. The copolymers are those obtained with compatible and bio-absorbable comonomers, for example lactic acid or lactide, its optically active forms and its analogs. Preferably, the copolymers based on glycolic acid, used as reinforcement elements, contain, in number of patterns, at least 90% patterns derived from glycolic acid.

Such polymers can be prepared in accordance with processes that are similar to those described, for example, in U.S. Pat. No. 2,676,945 and No. 3,297,033;

(4) the reinforcement elements embedded in the matrix are in the form of fibers, of threads, of films, of tissues, of plaits or of poles. It is essential that these elements be well embedded in the matrix, so as not to appear at the surface of the osteosynthesis part. They must thus be displaced from that surface;

(5) the concentration of the reinforcement elements varies from 5 to 50%, and in particular from 10 to 40% by weight, in relation to the total weight of the osteosynthesis part;

(6) the said osteosynthesis parts contain a charge composed of products that contain one, at least, of the following ions: calcium, magnesium, sodium, potassium, phosphate, borate, carbonate and silicate, the said charge being, preferably, at a concentration of 0.5 to 5% by weight of the total weight of the osteosynthesis part.

As indicated above, osteosynthesis parts with a PGA base have been known before.

However, PGA deteriorates quite rapidly after implantation into the organism. It has been observed that very clear signs of attack have occurred within 2 weeks. Consequently, PGA cannot provide any absolute assurance of reliable support, i.e. maintain excellent mechanical properties, and in particular resistance to shock, for a long enough time to guarantee repair of the skeleton parts of heavy mammals.

Polylactic acid (PLA), in particular L-polylactic acid, constituted by high molecular weight polymers, is a good plastic material, comparable to the best customary plastics, even in normally humid atmosphere, provided the low molecular weight products are eliminated and prolonged subjection to high temperature is avoided. Under such conditions, PLA is a good, biocompatible plastic. It is bio-absorbable, but much more slowly than PGA. In particular, it maintains a great part of its mechanical properties for at least two months.

It is less crystalline than PGA and has, therefore, better shock resistance and is consequently comparable to plastics that are recognized as being resilient.

Finally, PLA has a melting point of 175° C., i.e. clearly below that of PGA (220° C.) or of the latter's polymers with low comonomer content (207° C., for example, for the 10% lactide copolymer).

Therefore, by reinforcing a PLA matrix with PGA threads or other reinforcements, maximum benefit is derived from their respective properties, while avoiding the drawbacks: PLA contributes sufficient basic resilience and a good in vivo stability, while PGA reinforces the matrix without being impaired or damaged during casting, which is most important, and it is protected from the living milieu where it is easily attacked.

Further it has been noticed that when during the degradation of PGA reinforcements initially embedded in the matrix were becoming apparent, the degradation rate of the remaining matrix was increased.

In this manner, the following advantages are obtained:

(a) a matrix which does not deteriorate the tissues or the biodegradable reinforcement elements (fibers, pole, etc.), the latter having a much higher melting point, and thus being only slightly thermally degraded by casting, which insures the efficaciousness of the reinforcement;

(b) composite parts which maintain a high proportion of their resilience to shock, even after two months of implantation in vivo;

(c) parts whose resilience and tensile strength are much greater than those of parts that are not a composite of PLA and PGA;

(d) parts that can be cast or machined from elements cast at temperatures close to the melting point of poly-L-lactide (175° C.) by compression with fast cooling, which limits considerably the thermal degradation which causes the appearance of short chains whose end groups are favorable to degradation by hydrolysis, both in air and in vivo;

(e) parts whose matrix is constituted by a material containing few low molecular weight polymers, because these are physically eliminated prior to utilization and because their formation by degradation at casting is avoided and because their formation is minimized;

(f) parts whose shock resistance is considerably enhanced by the fact that the reinforcement tissue is initially protected against the biological environment, and by the fact that the matrix and the reinforcement adhere to one another in a satisfactory manner owing to impregnation;

(g) parts that are sterilizable at low temperature by ethylene oxide, which constitutes the best method in the present case, and particularly a less degradational one, contrary to methods using heat or ionizing irradiation;

(h) parts that can be handled in air or even in humid atmosphere at ambient temperature without special precautions for the normal duration of surgical interventions.

The advantages offered by these reinforced parts are very great, particularly for plates and nails used for osteosynthesis in cases where they are subjected to bending and shock.

The invention also relates to a process for preparing an osteosynthesis part as defined above, comprising providing alternating layers of the polymer constituting the matrix and the reinforcement elements, compressing the thus arranged alternating layers under sufficient pressure, such as about 20-500 kg/cm², at a suitable temperature which may vary between about 170° and 200° C., for a few minutes, preferably below about 7 minutes, and generally between about 30 sec and 7 minutes, in order to give the resulting composite the desired shape and dimension, and then rapidly cooling the thus formed composite and unmolding the same when the temperature thereof is below 50° C.

It will be apparent that the casting conditions utilized in the present invention can depend on three variables which should be balanced, i.e. pressure, temperature and heating time. In the present invention, it is important to limit the stay time for the polymers at high temperature, in order to prevent or minimize their degradation. The operation should also be carried out at the lowest possible temperature, naturally however taking into account the compression capacity of the mold used.

The invention also relates to the use of the osteosynthesis parts, as defined above, such use comprising putting the osteosynthesis part in place, in accordance with known methods, so as to reinforce a fractured or weakened bone in an animal or a human.

DETAILED DESCRIPTION OF THE INVENTION

The following non-limiting examples illustrate the present invention. Unless otherwise stated, all parts and percentages are by weight.

EXAMPLE 1

Preparation of poly-L-lactic acid

L-lactide monomer is purified by recrystallization in ethyl acetate, then in acetone, until a specific rotary power $[\alpha]_{589}^{25}$ at least equal to $-300°$ (solution in benzene) is achieved.

The monomer and a catalyst, (Zn powder in an amount of 0.05% by weight relative to the weight of the monomer) are placed in the polymerization reactor. By means of a vacuum pump, gas removal is then very carefully effected (1 to 2 mm Hg), and nitrogen or argon is used three times for purging. The reactor is sealed under vacuum and then heated at 140° C. for 20 days, making sure that the liquid is stirred as long as the viscosity of the milieu permits it. After total cooling, the polymer mass is reduced to shavings that are a few tenths of a millimeter thick so as to proceed to a solid-liquid extraction with acetone for 24 hours. The polymer, rid of the low molecular weight products, is dried for 48 hours in a vacuum drying-oven at 50° C. Finally, it is kept sealed against humidity.

EXAMPLE 2

Casting of a part with PGA reinforcement

The biodegradable reinforcement (fabric, dressing, strand . . . ) is impregnated for 1 hour with a solution of chloroform containing 10% of PLA. Then it is dried under vacuum at 40° C. for 24 hours in order to eliminate the solvent and any trace of humidity.

The PLA (matrix) and the reinforcement elements are placed in alternating layers into a pressure mold preheated to 190° C. The dimensions of the reinforcement elements, as well as their position in the matrix, are selected in such a manner that they are completely embedded in the matrix. Then, pressure is applied slowly, increasing it to a level of 200 kg/cm² in one minute. That pressure is applied for 2 minutes, the temperature being kept constant at 190° C. Finally, the whole is cooled rapidly, and is unmolded when the temperature falls below 50° C.

Using this mode of operation, a part reinforced by a biodegradable fabric is thus cast. The fabric, made of polyglycolic threads with a diameter of 0.1 mm, is marketed by Lederle Laboratories—Davis & Geck under the tradename "DEXON".

The warp is constituted by threads having a 1 mm interval between them, whereas the woof is made of contiguous threads.

Alternating layers of PLA powder, obtained in accordance with example 1, and of reinforcing fabric, are placed in a compression mold.

After compression, a disc of 6 mm thickness is obtained, from which two notched IZOD samples are cut.

The resilience of the material thus obtained, has been measured. It is equal to 90 kg·cm/cm$^2$.

EXAMPLE 3

Molding of a part charged with tricalcium phosphate and reinforced with PGA fibers Powdered tricalcium phosphate is dried at 60° C. for 24 hrs. Some PLA, obtained as in example 1, is placed in a ball bearing crusher, and then tricalcium phosphate, in a concentration of 1% by weight of the weight of PLA. Crushing is carried out for 10 minutes. The mixture obtained is then dried under reduced pressure at 40° C. for 24 hours.

Finally, a composite part is prepared, using the process described in example 2, employing as the polymer the PLA charged with tricalcium phosphate. The part was given the shape of an osteosynthesis plate with the appropriate dimensions.

EXAMPLE 4

Preparation of osteosynthesis nails

These nails, of conventional shape and dimensions, are prepared by molding in accordance with a process similar to that of Example 2.

The matrix is made of PLA obtained as in Example 1. The reinforcement element is constituted by PGA fabric formed into a tube. The tube is placed so as to be entirely embedded in the PLA of the matrix.

Osteosynthesis nails have also been made where the reinforcement element is constituted by PGA fibers disposed in a spiral.

What is claimed is:

1. An osteosynthesis part, in the shape of a three-dimensional solid, and made of a bio-compatible, absorbable polymer, comprises composite parts constituted by a matrix of polylactic acid or a copolymer thereof; said copolymer comprising at least 90% of units derived from lactic acid, said matrix containing a reinforcement element in the shape of fibers, threads, films, fabrics, or strands embedded therein and present in an amount of 5 to 50% by weight based on the total weight of the osteosynthesis part, said element being made of polyglycolic acid or a copolymer thereof, and containing optionally a charge capable of stimulating the absorption of the polymer for the benefit of a newly formed tissue.

2. The osteosynthesis part of claim 1, wherein the matrix is a polymer of D-lactic acid, or L-lactic acid, said polymer exhibiting high enantiomorphous purity.

3. The osteosynthesis part of claim 1, wherein the matrix is a biodegradable copolymer of lactic acid and a compatible comonomer.

4. The osteosynthesis part of claim 3, wherein the said copolymer contains 95% of units derived from lactic acid.

5. The osteosynthesis part of claim 3, wherein said comonomer is selected from the group consisting of α-hydroxy acid derivative, and α-amino acid derivative.

6. The osteosynthesis part of claim 1 wherein the said matrix is obtained initially from a polylactic acid or a copolymer thereof, having a high molecular weight, such that the mean molecular weight is greater than or equal to 80,000.

7. The osteosynthesis part of claim 6, wherein said molecular weight is greater than or equal to 100,000.

8. The osteosynthesis part of claim 1 wherein the reinforcement element is constituted by a polymer having a molecular weight greater than or equal to 10,000.

9. The osteosynthesis part of claim 8, wherein the said molecular weight is between 10,000 and 100,000.

10. The osteosynthesis part of claim 1, wherein the reinforcement element is made of polyglycolic acid.

11. The osteosynthesis part of claim 1, wherein the reinforcement element is constituted by a copolymer of polyglycolic acid and a compatible and bio-absorbable comonomer.

12. The osteosynthesis part of claim 11, wherein the said comonomer is selected from the group consisting of lactic acid or lactide, and the optically active forms and analogs thereof.

13. The osteosynthesis part of claim 11, wherein said reinforcement element is made from a glycolic acid copolymer containing at least 90% of units derived from glycolic acid.

14. The osteosynthesis part of claim 1, wherein it is in the form of a plate, a nail, a screw, or a solid block to be molded or machined.

15. The osteosynthesis part of claim 1 containing a charge constituted by a material containing at least one ion selected from: calcium, magnesium, sodium, potassium, phosphate, borate, carbonate and silicate.

16. The osteosynthesis part of claim 15, wherein the charge is present in an amount of 0.5 to 5% by weight based on the total weight of the osteosynthesis part.

17. Use for the osteosynthesis part of claim 1 comprising putting said osteosynthesis part in place so as to reinforce a fractured or weakened bone of a human or animal subject.

18. An osteosynthesis part, in the shape of a three-dimentional solid, and made of a bio-compatible, absorbable polymer, consisting of a homopolymerized polylactic acid matrix having embedded therein a reinforcement element made of polyglycolic acid and containing a charge capable of stimulating the absorption of the polymer for the benefit of newly formed tissue.

19. The osteosynthesis part of claim 18 wherein said reinforcement element is present in an amount of 5 to 50% by weight based on the total weight of the osteosynthesis part.

20. An osteosynthesis part, in the shape of a three-dimensional solid, and made of a bio-compatible, absorbable polymer, consisting of a homopolymerized polylactic acid matrix having embedded therein a reinforcement element made of polyglycolic acid or a copolymer thereof, said reinforcement element being present in an amount of 5 to 50% by weight based on the total weight of the osteosynthesis part.

21. The osteosynthesis part of claim 20 wherein said polymer also includes a charge capable of stimulating the absorption of the polymer for the benefit of a newly formed tissue.

* * * * *